United States Patent
Wiersma

[11] Patent Number: 5,948,414
[45] Date of Patent: Sep. 7, 1999

[54] HERBAL BASED NASAL SPRAY

[75] Inventor: Jack G. Wiersma, Palm Beach Gardens, Fla.

[73] Assignee: Nouveau Technologies, Inc., Tequesta, Fla.

[21] Appl. No.: 09/047,265

[22] Filed: Mar. 24, 1998

[51] Int. Cl.$^6$ .................................................. A61K 9/08
[52] U.S. Cl. ................... 424/400; 424/434; 424/195.1; 514/853; 514/391; 514/653
[58] Field of Search .................. 424/400, 434, 424/195.1; 514/853, 391, 653

[56] References Cited

U.S. PATENT DOCUMENTS

| | | |
|---|---|---|
| 5,175,152 | 12/1992 | Singh . |
| 5,376,637 | 12/1994 | Sawai et al. . |
| 5,468,492 | 11/1995 | Szaloki et al. . |
| 5,648,358 | 7/1997 | Mitra . |

FOREIGN PATENT DOCUMENTS

| | | |
|---|---|---|
| 0 666 078 | 8/1995 | European Pat. Off. . |
| 62-223131 | 1/1987 | Japan . |
| 62-207226 | 9/1987 | Japan . |

OTHER PUBLICATIONS

"Saponinum depuratum levissium Q" Analytical data, Dr. H. Schmittman GmbH, Mar. 1989, cover sheet, intro. p., standards page.

Certificate of Analyses—Saponin DAB–9, Dr. H. Schmittmann, GmbH, Aug. 12, 1997.

Material Safety Data Sheets13 "Saponine–DAB–9" Dr. Ha Schmittmann GmbH, Jan. 1, 1997.

*Primary Examiner*—Thurman K. Page
*Assistant Examiner*—Brian K. Seidleck
*Attorney, Agent, or Firm*—McHale & Slavin PA.

[57] ABSTRACT

This invention relates to an improved herbal-based decongestant and antihistamine nasal spray which includes known constituents in specific ratios and further includes a saponin. The invention further relates to a method for treating nasal congestion which results in enhanced decongestant action and surprising curative effects.

24 Claims, No Drawings

HERBAL BASED NASAL SPRAY

FIELD OF THE INVENTION

This invention relates to an improved herbal-based decongestant and antihistamine nasal spray which includes known constituents in specific ratios and further includes a saponin.

BACKGROUND OF THE INVENTION

Today there are numerous commercial products that contain both an antihistamine and decongestant. These products may have less tendency to cause sedation because of the decongestant factor and thereby can offset, in some cases, the sedative aspect of the antihistamine. It has been further determined that these products vary substantially in their duration of action thereby offering inconsistent results to the public at large.

Although it is known that antihistamines do not prevent or cure the common cold they are found in many cold remedies. As stated in the "Handbook of Non-Prescription Drugs, 9th edition," "Antihistamines are chemical agents that exert their effect in the body primarily by competitively blocking the actions of histamine at receptor sites. Those antihistamines that block the $H_1$ receptor are potentially useful treating allergic rhinitis and, to a lessor extent, colds."

Some of the most commonly used non-prescription antihistamines are selected from the group consisting of brompheniramine maleate, chlorpheniramine maleate, doxylamine succinate, phenindamine tartrate, pheniramine maleate, promethazine maleate, pyrilamine maleate, thonzylamine hydrochloride, and mixtures thereof. These compounds are recognized by the Food and Drug Administration (FDA) over-the-counter (OTC) advisory review panel on cold, cough, allergy, bronchodilator, and antiasthmatic drug products as being safe for non-prescription use and effective in suppressing the symptoms of allergic rhinitis when taken in the dosage specified. Among the above-mentioned non-prescription antihistamines it is known that chlorpheniramine maleate possesses relatively weak sedative properties. Due to its weak sedative properties chlorpheniramine maleate enjoys widespread use in numerous combination decongestant/antihistamine products.

Decongestants, when applied intra-nasally, are known to provide relief of nasal congestion. This decongestant action is accomplished by the shrinking of the mucous membrane which makes the breathing process easier along with allowing the sinus cavities to drain.

As with antihistamines there are recognized decongestants for (OTC) products such as those selected from the group consisting of naphazoline hydrochloride, ephedrine, oxymetazoline hydrochloride, phenylephrine hydrochloride, xylometaxoline hydrochloride and mixtures thereof. The FDA advisory review panel on cold, cough, allergy bronchodilator, and antiasthmatic drug products has recommended these ingredients as safe and effective at appropriate recommended controlled dosage rates.

Additionally, many other ingredients have been added to cold products which fall into the category of aromatics composed primarily of natural oils or extracts therefrom such as camphor, eucalyptus oil, menthol, azulen and mixtures thereof.

With many antihistamine and decongestant products a preservative is required to insure the stability of the finished product. Benzalkonium chloride has been found to be used in many pharmaceutical preparations and is recognized as safe when used at the recommended and used dosage rates.

Several problems have heretofore plagued the field of antihistamine/decongestant nasal sprays. One problem is a failure of the formulations to provide relief for a desired time interval. This results in misuse of the formulations in the form of overdosing. This leads to the second problem which is termed "rebound congestion". This is a phenomenon which occurs when, largely due to overdosing or a prolonged usage period, acute nasal congestion manifests itself as the effects of the antihistamine/decongestant diminish.

It is therefore an object of the present invention to formulate an antihistamine and decongestant that optimizes the desired prompt and prolonged effect.

It is a further object of the invention to formulate an enhanced antihistamine/decongestant nasal spray that does not provoke rebound congestion.

It is a still further object of the invention to provide a method for treating nasal congestion which results in enhanced decongestant action and surprising curative effects.

Yet another object of the invention is to provide a method of treating rhinitis or sinusitis by incorporating the novel compositions of the invention into a container adapted to deliver a controlled dosage amount, for example via a spray or a specific number of drops. The controlled dosage amount is calculated so as to be effective to administer the required ingredients within their prescribed parameters of use when said controlled dosage amount is applied to the effected nasal and sinus passages.

Other objects and advantages of this invention will become apparent from the following description.

SUMMARY OF THE INVENTION

The instant invention is directed to a composition containing pharmaceutically effective amounts, as said amounts relate to a nasal spray, of a decongestant, an antihistamine, a preservative, an aromatic, an emulsifier and an adjuvant; and to a method of use thereof. In use the composition is diluted to useful concentrations via the inclusion of water, preferably purified waters such as filtered, distilled, sterilized and demineralized water. In a preferred embodiment, demineralized water is utilized. It is known that the mucus film found in the nasal passageways plays an important part in the bodies defense mechanism by the constant beating of the cilia, whereby movement of this film toward the nasopharynx is accomplished, carrying with it trapped particles to be expectorated or swallowed. This mucus film is rich in lysozymes and contains glycoproteins and immunoglobulins. Lysozymes are an important defense against bacteria because they easily digest the lipid and carbohydrate cell walls of some bacteria and are responsible for the digestion of the cell walls of pollens and the subsequent release of antigenic substances. It is with this fact in mind that the inventor has added a specific amount of a triterpene saponin to the composition being discussed. By the addition of the triterpene saponin to the composition a surprising effect has been determined. Inclusion of triterpene saponin enhances the benefit of the antigenic substances produced by the action of the lysozymes contained in the mucus film found in the nasal passages.

In a preferred embodiment, the instant invention is defined as a composition comprising, in combination, effective amounts, as recommended for a nasal spray environment, of a decongestant commonly referred to as naphazoline hydrochloride; a preservative commonly referred to as benzalkonium chloride; an antihistamine commonly referred to as chlorpheniramine maleate; an aromatic material selected from the group consisting of menthol, azulen, camphor, eucalyptus oil and mixtures thereof; an emulsifier, which broadly comprises a chemical dispersing agent and which is preferably selected from the class of emulsifiers containing a combination of hydrophobic and hydrophilic substituents, particularly a combination of glycerol-polyethylene glycol ricinoleate, fatty acid esters of polyethyleneglycol and polyethylene glycol and ethoxylated glycerol, and, in a most preferred embodiment comprises an emulsifying agent available from BASF Aktiengesellschaft and marketed under the tradename CREMOPHOR EL; an adjuvant commonly referred to as triterpene saponin that carries the equivalent of a DAB-9 purity rating as set forth by the German government; and water, preferably demineralized water.

The composition of the instant invention, utilizing FDA approved components, is unique in that the individual components, when incorporated at specific ratios of the total product, offer an improved antihistamine and decongestant product that delivers the prompt and prolonged desired effects heretofore not achievable.

DETAILED DESCRIPTION OF THE PREFERRED EMBODIMENT

Since the instant invention has a two-fold purpose, namely an antihistamine and a decongestant, the detailed description of the composition will be first described by the antihistamine portion of the composition followed by the decongestant portion of the composition. Subsequent to the above, the appropriate combined elements will be defined.

As stated earlier, antihistamines are potentially useful in treating allergic rhinitis and colds. Although the invention contemplates the inclusion of any known antihistamine, for purposes of example the instant invention is characterized by using chlorpheniramine maleate, which is recognized by the Food and Drug Administration (FDA) over-the-counter (OTC) advisory review panel on cold, cough, allergy, bronchodilator, and antiasthmatic drug products. Additionally, it is known in the industry that chlorpheniramine maleate possesses weak sedative properties. This characteristic is most important when considering a nasal decongestant and antihistamine product. Intranasal application of chlorpheniramine maleate, as further described in this invention, provides prompt and dramatic decrease in nasal congestion while permitting the sinus cavities to drain. This improves the breathing process. The combination decongestant/antihistamine of the instant invention will also cause less tendency towards drowsiness.

It is known that chlorpheniramine maleate has the following dosage recommendations over a 24 hour period as established by the Food and Drug Administration (FDA):

|  | Adults | Children 6 < 12 years | Children 2 < 6 years |
| --- | --- | --- | --- |
| Chlorpheniramine maleate | 4 mg every 4–6 Hrs (24 mg/day) | 2 mg every 4–6/ 4–6 Hrs. (12 mg/day) | 1 mg every 4–6 Hrs. (6 mg/day) |

The compatibility of chlorpheniramine maleate within the body of this invention, at the recommended inclusion rate to the total composition, has been clearly demonstrated in clinical trials.

Although the invention contemplates the inclusion of any known decongestant, for purposes of example the instant invention is characterized by using the decongestant naphazoline hydrochloride. Naphazoline hydrochloride is recognized as a topical nasal decongestant whose characteristics show it to be a powerful vasoconstrictor. It is generally administered as 1 or 2 drops or sprays of a 0.05% solution every 6 hours. Naphazoline hydrochloride is recognized by the Food and Drug Administration (FDA) over-the-counter (OTC) advisory review panel on cold, cough, allergy, bronchodilator, and antiasthmatic products.

It is known that naphazoline hydrochloride has the following dosage recommendations:

| Concentration | Adults | Children 6 < 12 | Children 2 < 6 |
| --- | --- | --- | --- |
| Naphazoline 0.05% | 1–2($\geq$6 hours) sprays/drops | not recommended Refer to 0.025%) 1–2 ($\geq$6 hours) sprays/drops | — |

It is further known that many cold products today contain varying amounts and combinations of aromatic materials, such as camphor, eucalyptus oil, menthol, and occasionally the natural extract of the camomile plant oil, azulen. These ingredients, at safe and specific inclusion rates, are found in the instant invention as aromatics. Additionally, but not wishing to be limited thereto, the FDA approved preservative benzalkonium chloride, commonly used in the industry, may be utilized as the preservative of choice in this invention, when such inclusion is necessary.

It has been determined that to effectively incorporate the above-mentioned components of this invention into a complete composition one will need to utilize an emulsifier. The instant invention prefers, for this purpose, the BASF product CREMOPHOR EL. CREMOPHOR EL is known in the industry to be used as an emulsifying agent for the pharmaceuticals, cosmetics and feedstuffs industries and is used in aqueous preparation of hydrophobic substances, e.g. fat soluble vitamins and essential oils. Although CREMOPHOR EL is a recognized emulsifying agent, the inventor has only found one referenced use in a nasal decongestant/ antihistamine composition. Therefore, one skilled in the art could assume that its use in the instant invention is within the realm of feasibility and yet somewhat unknown as it relates to the above-mentioned application.

By example, a solution of one part of azulen in about four parts of CREMOPHOR EL can be infinitely diluted with water. It has been determined that the use of CREMOPHOR EL with the above-mentioned components, utilizing a pure, preferably a demineralized water, does under precise formulation procedures, offer the optimum emulsion desired along with the stability required for an effective herbal-based nasal spray decongestant/antihistamine product.

It has been stated by various literature references, e.g. Abbott Laboratories to White, JA. Paranasal Sinus infections; Ballenger, JJ. Diseases of the nose, throat, ear, head, and neck. Philadelphia, Pa.: Lea & Febiger: 1991: chap. 11. that "a cold or pharyngitis can cause nasal passageways to swell, block normal drainage, and trap bacteria in the sinus cavities where they multiply and cause inflammation. Energetic nose-blowing during a cold can also contribute to sinusitis by forcing bacteria from the nose into the sinus cavities." It is known that chronic sinusitis can last up to three months or more and can be caused by acute infections.

Additionally, the mucus film found in the nasal passageways plays an important part in the bodies defense mechanism by the constant beating of the cilia, whereby movement of this film toward the nasopharynx is accomplished, carrying with it trapped particles to be expectorated or swallowed. This mucus film is rich in lysozymes and contains glycoproteins and immunoglobulins. Lysozymes are an important defense against bacteria because they easily digest the lipid and carbohydrate cell walls of some bacteria and are responsible for the digestion of the cell walls of pollens and the subsequent release of antigenic substances. It is with this fact in mind that the inventor has added a specific amount of a triterpene saponin to the composition being discussed. By the addition of the triterpene saponin to the composition a surprising effect has been determined. Inclusion of triterpene saponin enhances the benefit of the antigenic substances produced by the action of the lysozymes contained in the mucus film found in the nasal passages.

Further, as evidence of this action a prominent medical physician who leads a nationally recognized preventative health care clinic has made the following observations: . . . after clinical observations on many people he stated at the outset there was no other product in a nasal spray on the market as effective (healing) as this herbal-based nasal spray. He found it especially effective in patients with chronic sinusitis who have had sinus problems for years and may be cured of that chronic problem with this nasal spray. This herbal-based nasal spray was found also to be extremely effective in the chronic rhinitis or nasal problems where people have crusting of their nose, bleeding, and chronic infection and irritation. He states that this herbal-based nasal spray remarkably clears up these problems. Further "this herbal based product has a definite place in the adjunctive treatment of upper respiratory infection, including nose and sinuses . . . it acts instantly and there is no rebound".

These observations, including the surprising effect, were based on the use of the afore-mentioned components in an aqueous composition in the following amounts:

| 1. | Menthol | 3.2 | grams* |
|---|---|---|---|
| 2. | Camphor | 6.0 | grams* |
| 3. | Eucalyptus Oil | 3.3 | grams* |
| 4. | CREMOPHOR EL | 31.5 | grams |
| 5. | Triterpene Saponin (DAB-9 Grade) | 1.5 | grams |
| 6. | Naphazoline Hydrochloride | 1.5 | grams |
| 7. | Chlorpheniramine Maleate | 6.0 | grams |
| 8. | Benzalkonium Chloride | 1.2 | grams |
| 9. | Azulen 25% (water soluble) | 6.3 | grams* |

*indicates those etheric oils that may evaporate during the preparation process.

Subsequent to formulation, the above component quantities were then diluted with demineralized water to a total volume of about 3000 ml.

The amounts of the above ingredients may be varied, up or down, by up to about 10% without adversely effecting the efficacy of the product. Such differences are permitted following GMP (Good Manufacturing Practices) in the event that the production procedure requires it.

Additionally, based on numerous observations of nasal spray products containing varying quantities of commercially available ingredients, the basic differences of those products with respect to the instant invention are that the heretofore commercially available antihistamine/decongestant nasal sprays generally require applications approximately every four hours and in most cases offer only temporary relief. The instant invention however, has surprisingly been found to be effective with applications approximately every six hours and with use causes a curative and healing effect which is beyond temporary relief.

While not wishing to be bound to any particular, the inventor is convinced that the curative effect is directly related to the specific combination of ingredients along with the triterpene saponin's positive reaction with the antigenic substances caused by the action of the lysozymes within the nasal cavity. This reaction is thought to basically enhance the antigenic substances ability to effect antibodies which in most instances are produced during exposure to an antigen, such a response being termed active immunity.

Further, it is known in the art, that an antigen, when introduced into the body, induces an immune response including production of specific antibodies. Therefore, the instant invention is unique in the industry not only in the duration of its effectiveness between applications but additionally in its curative effect under observation.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification.

What is claimed is:

1. A nasal spray composition comprising in combination pharmaceutically effective amounts of:

a decongestant selected from the group consisting of naphazoline hydrochloride, ephedrine, oxymetazoline hydrochloride, phenylephrine hydrochloride, xylometaxoline hydrochloride and mixtures thereof;

an antihistamine selected from the group consisting of brompheniramine maleate, chlorpheniramine maleate, doxylamine succinate, phenindamine tartrate, pheniramine maleate, promethazine maleate, pyrilamine maleate, thonzylamine hydrochloride, and mixtures thereof;

an aromatic selected from the group consisting of natural oils or extracts therefrom such as camphor, eucalyptus oil, menthol, azulen and mixtures thereof;

an emulsifier selected from the class of emulsifiers containing a combination of hydrophobic and hydrophilic substituents, particularly a combination of glycerolpolyethylene glycol ricinoleate, fatty acid esters of polyethyleneglycol and polyethylene glycol and ethoxylated glycerol;

a triterpene saponin adjuvant; and water.

2. The composition according to claim 1, wherein the water is demineralized water.

3. The composition according to claim 1, further including a preservative.

4. The composition according to claim 3, wherein the preservative is benzalkonium chloride.

5. A composition useful as a nasal spray comprising in combination:

| Menthol | about | 2.88–3.52 | grams |
|---|---|---|---|
| Camphor | about | 5.4–6.6 | grams |
| Eucalyptus Oil | about | 2.97–3.63 | grams |
| Chemical dispersing agent | about | 28.35–34.65 | grams |
| Triterpene Saponin | about | 1.35–1.65 | grams |
| Naphazoline Hydrochloride | about | 1.35–1.65 | grams |
| Chlorpheniramine Maleate | about | 5.4–6.6 | grams |
| Azulen 25% (water soluble) | about | 5.67–6.93 | grams | and wherein the composition is diluted with water to a total volume of about 3000 ml.

6. The composition according to claim 5, wherein the water is demineralized water.

7. The composition according to claim 5, further including a preservative.

8. The composition according to claim 7, wherein the preservative is benzalkonium chloride.

9. A composition useful as a nasal spray comprising in combination:

| | | | |
|---|---|---|---|
| Menthol | about | 3.2 | grams |
| Camphor | about | 6.0 | grams |
| Eucalyptus Oil | about | 3.3 | grams |
| Chemical dispersing agent | about | 31.5 | grams |
| Triterpene Saponin | about | 1.5 | grams |
| Naphazoline Hydrochloride | about | 1.5 | grams |
| Chlorpheniramine Maleate | about | 6.0 | grams |
| Azulen 25% (water soluble) | about | 6.3 | grams | and wherein the composition is diluted with water to a total volume of about 3000 ml.

10. The composition according to claim 9, wherein the water is demineralized water.

11. The composition according to claim 9, further including a preservative.

12. The composition according to claim 9, wherein the preservative is benzalkonium chloride.

13. A method for the treatment of rhinitis and sinusitis with the composition defined by claim 1 comprising:

incorporating the composition into a container adapted to deliver a controlled dosage amount; and applying said controlled dosage amount to the effected nasal and sinus passages.

14. A method for the treatment of rhinitis and sinusitis with the composition defined by claim 2 comprising:

incorporating the composition into a container adapted to deliver a controlled dosage amount; and applying said controlled dosage amount to the effected nasal and sinus passages.

15. A method for the treatment of rhinitis and sinusitis with the composition defined by claim 3 comprising:

incorporating the composition into a container adapted to deliver a controlled dosage amount; and applying said controlled dosage amount to the effected nasal and sinus passages.

16. A method for the treatment of rhinitis and sinusitis with the composition defined by claim 4 comprising:

incorporating the composition into a container adapted to deliver a controlled dosage amount; and applying said controlled dosage amount to the effected nasal and sinus passages.

17. A method for the treatment of rhinitis and sinusitis with the composition defined by claim 5 comprising:

incorporating the composition into a container adapted to deliver a controlled dosage amount; and applying said controlled dosage amount to the effected nasal and sinus passages.

A method for the treatment of rhinitis and sinusitis with the composition defined by claim comprising: incorporating the composition into a container adapted to deliver a controlled dosage amount; and applying said controlled dosage amount to the effected nasal and sinus passages.

18. A method for the treatment of rhinitis and sinusitis with the composition defined by claim 6 comprising:

incorporating the composition into a container adapted to deliver a controlled dosage amount; and applying said controlled dosage amount to the effected nasal and sinus passages.

19. A method for the treatment of rhinitis and sinusitis with the composition defined by claim 7 comprising:

incorporating the composition into a container adapted to deliver a controlled dosage amount; and applying said controlled dosage amount to the effected nasal and sinus passages.

20. A method for the treatment of rhinitis and sinusitis with the composition defined by claim 8 comprising:

incorporating the composition into a container adapted to deliver a controlled dosage amount; and applying said controlled dosage amount to the effected nasal and sinus passages.

21. A method for the treatment of rhinitis and sinusitis with the composition defined by claim 9 comprising:

incorporating the composition into a container adapted to deliver a controlled dosage amount; and applying said controlled dosage amount to the effected nasal and sinus passages.

22. A method for the treatment of rhinitis and sinusitis with the composition defined by claim 10 comprising:

incorporating the composition into a container adapted to deliver a controlled dosage amount; and applying said controlled dosage amount to the effected nasal and sinus passages.

23. A method for the treatment of rhinitis and sinusitis with the composition defined by claim 11 comprising:

incorporating the composition into a container adapted to deliver a controlled dosage amount; and applying said controlled dosage amount to the effected nasal and sinus passages.

24. A method for the treatment of rhinitis and sinusitis with the composition defined by claim 12 comprising:

incorporating the composition into a container adapted to deliver a controlled dosage amount; and applying said controlled dosage amount to the effected nasal and sinus passages.

* * * * *